United States Patent [19]

Donnerhack et al.

[11] Patent Number: 4,880,003

[45] Date of Patent: Nov. 14, 1989

[54] CABIN FOR CARRYING OUT CRYOTHERAPY

[75] Inventors: Andreas Donnerhack, Krefeld; Klemens Thoma, Krefeld-Huls; Wolfgang Volker, Tonisvorst; Thomas Stratz; Rolf-Dieter Gallmeister, both of Bad Säckingen, all of Fed. Rep. of Germany

[73] Assignee: Messer. Griesheim, Fed. Rep. of Germany

[21] Appl. No.: 205,510

[22] Filed: Jun. 3, 1988

Related U.S. Application Data

[63] Continuation of Ser. No. 907,321, Sep. 11, 1986, abandoned.

[30] Foreign Application Priority Data

Sep. 28, 1985 [DE] Fed. Rep. of Germany ....... 3534630

[51] Int. Cl.[4] ............................................. A61H 33/06
[52] U.S. Cl. .................................... 128/374; 128/367; 128/371; 128/DIG. 27
[58] Field of Search ............... 128/374, 371, 367, 373, 128/375, 368, 395, 396, DIG. 27

[56] References Cited

U.S. PATENT DOCUMENTS

| | | | |
|---|---|---|---|
| 1,563,736 | 12/1925 | Fink | 128/371 |
| 1,773,450 | 8/1930 | Dorment | 128/374 |
| 2,008,653 | 7/1935 | Braselton | 128/395 |
| 2,174,445 | 9/1939 | Oliver | 128/367 |
| 2,814,297 | 11/1957 | Stewart | 128/374 |
| 3,457,923 | 7/1969 | Johnston | 128/374 |
| 3,781,921 | 1/1974 | Rouat | 128/374 |
| 3,902,488 | 9/1975 | Sheppard | 128/367 |
| 4,044,772 | 8/1977 | Schloss | 128/371 |
| 4,149,529 | 4/1979 | Copeland et al. | 128/400 |
| 4,469,102 | 9/1984 | Fish | 128/396 |

FOREIGN PATENT DOCUMENTS

740945 11/1955 United Kingdom ............... 128/374

*Primary Examiner*—Michael Safavi
*Attorney, Agent, or Firm*—Connolly & Hutz

[57] ABSTRACT

A cabin for carrying out cryotherapy on the entire body with a cold treatment gas is made open from above. The distance from the upper edge of the cabin walls to the floor can be adjusted to the height of the patient's neck.

12 Claims, 2 Drawing Sheets

© 1
CABIN FOR CARRYING OUT CRYOTHERAPY

CROSS REFERENCE TO RELATED APPLICATION

This application is a continuation of Ser. No. 907,321, filed Sept. 11, 1986 and now abandoned.

Aside from the local cryotherapy carried out since a few years ago with a cold treatment gas, e.g. for treatment of rheumatic diseases, a cryotherapy on the entire body is also carried out with some forms of illnesses. Air is hereby cooled in heat exchangers, with the aid of liquid nitrogen, and injected into closed chamber. This chamber or cabin has walls of insulating material and connections for the supply and removal of the treatment gas. Such a chamber is, for example, disclosed in the Japanese utility patent No. 168 125/81. This concept finds little approval, however, from doctors as well as from patients. The reasons for this are manyfold. The patients object to the lack of direct contact with the doctor since during treatment, only an indirect contact through speaker arrangements is possible. The strong buildup of fog in the chamber further intensifies this impression of lack of direct contact. Another disadvantage is the undesirable cooling in the area of the patient's head. Aside from this one must, by special means, avoid the inhalation of cold air. Regardless of this, such chambers require a high investment cost. Because of the long buildup time, there is a need for continuous operation, as a result of which relatively high operation costs result. The supervision of the patient during treatment is expensive.

SUMMARY OF INVENTION

The objective of the invention is to provide a cabin for carrying out cryotherapy on the entire body with a cold treatment gas, which permits direct contact between physician and patient during treatment, which leaves the head of the patient free and which, because of shorter buildup times, does not require continuous operation.

In accordance with this invention the cryotherapy cabin is open at its top and has adjustable side walls for adjustment to the height of the patient.

THE DRAWINGS

DETAILED DESCRIPTION

Figure 1:
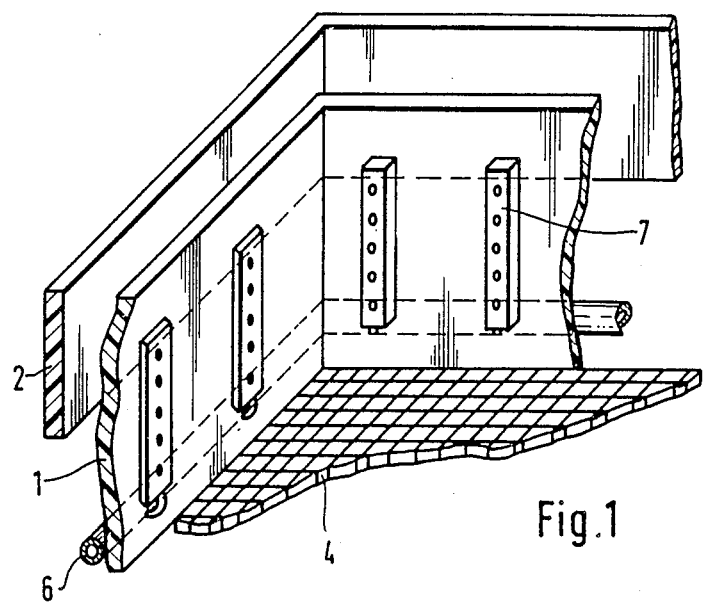
FIG. 1 is a partially broken up perspective view of a cabin with adjustable walls, in accordance with this invention.
Figure 2:
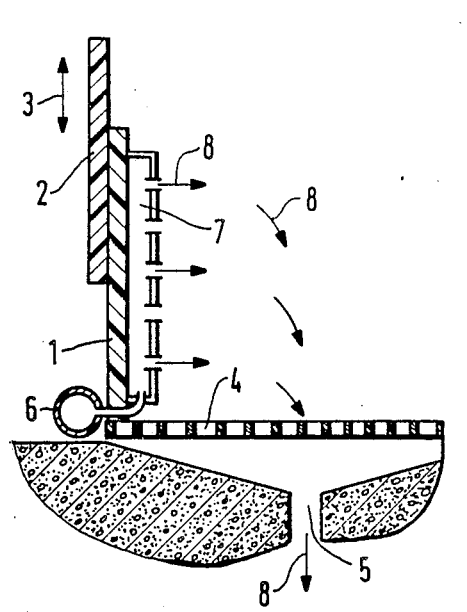
FIG. 2 is a cross section of a wall of the cabin according to FIG. 1.

The cabin depicted in FIGS. 1 and 2 is, according to the invention, open at the top and has height adjustable walls. The wall 1 is fixed and has a door (not shown) for entering the cabin. The wall 1 consists of insulating material, for example of a double walled insulating glaze made of plastic. The wall 2 forms the upper part of the cabin and can be shifted vertically by sliding it on the wall 1. The direction of this shift is indicated by an arrow 3. The wall 2 also has a door (not shown) for entering the cabin and is, likewise of insulating material.

The wall 2 can be shifted by any suitable means, in the simplest case, mechanically, by hand, whereby it can be stopped at various heights. The height adjustment can, however, occur with more expensive means such as hydraulic or electrical. For the treatment, the wall 2 is adjusted so that its upper edge is level with the neck of the patient. A grate 4 forms the floor of the cabin. Under the grate there is an outlet opening 5. The supply of cold treatment gas occurs, by means of a closed circuit line 6, in several nozzle strips 7 which are mounted vertically at regular interval over the perimeter of the cabin. The treatment gas is suctioned off via the outlet opening 5. The direction of flow is indicated by the arrow 8.

The cold wind is channeled into the cabin and directed at the patient by means of the nozzle strips. The suction at the floor of the cabin ensures that the cold wind stream is directed downward. Thus, it does not flow upward into the space/room and does not cause any fog formation there. A great advantage is that the treatment gas does not flow onto the patient's head. There is always a direct voice and visual contact between the physician and the patient during the treatment.

Figure 3:
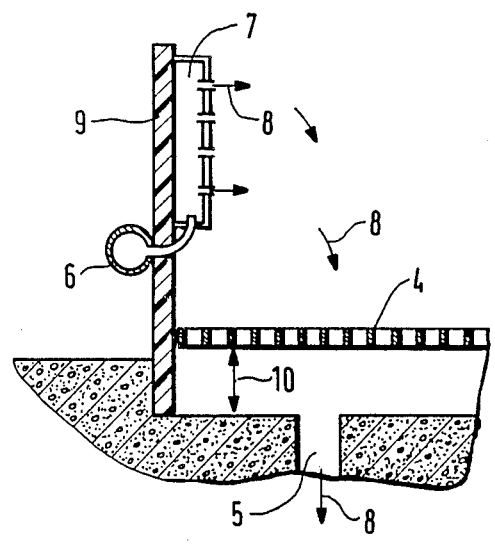
FIG. 3 is a cross section of a wall of a cabin with a height adjustable floor.

The embodiment shown in FIG. 3 differs from those shown in FIGS. 1 and 2 solely therein that, in this case, the grate 4 is height adjustable and, because of this, only one fixed wall 9 is provided. The capability of the height adjustment of the grate 6 is indicated by the arrow 10. Even here, the height adjustment can occur mechanically, by hand. Of course, more expensive mechanisms could also be used.

Figure 4:
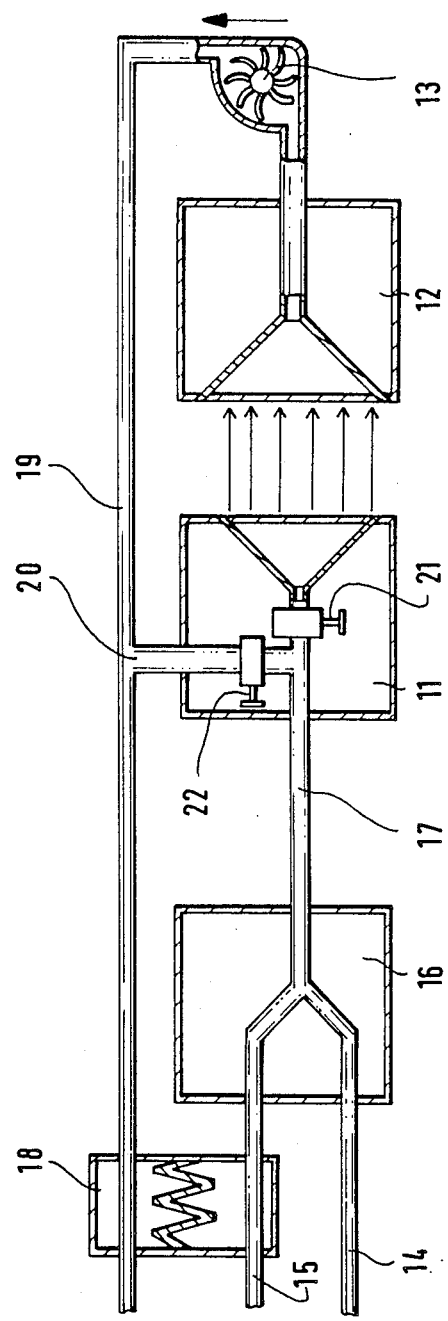
FIG. 4 is a device for producing the cold treatment gas permits the an economical idling operation of the cabin.

All common equipments and gas compositions can be used to form the treatment gas. The treatment gas is preferably formed by mixing dry air with a cold liquified gas, preferably nitrogen. This allows, in particularly simple manner, an economical idling operation of the cabin as is shown in FIG. 4. The cabin is schematically illustrated there, consisting of an entry section 11 and an exit section 12. The entry section thereby corresponds to the walls 1, 2 with the nozzle strips 7 while the exit section 12 corresponds to the grate 4 with the outlet opening 5. The suction blower 13 serves to recycle the treatment gas; the direction of the flow of gas is indicated by arrows without reference numerals. The cold treatment gas is formed from liquid nitrogen which is supplied via the line 14 and dry air which is supplied via the line 15. The formation of the treatment gas from these components occurs in a mixing device 16 from where it is fed to the entry section 11 via the line 17. The line 17 corresponds to the closed circuit line 6 in the FIGS. 1 to 3. Before entering the mixing device 16, the air flow through a heat exchanger 18. The suctioned treatment gas flowing back via line 19 also flows through the heat exchanger so that the entering air is precooled When idling, that is when no patient is being treated, the installation is kept in a ready state and cold treatment gas is channeled directly via line 20 back into the heat exchanger without passing through the cabin. the rerouting of the gas stream is accomplished by means of the valves 21 and 22. As a result of the economical idling operation, nitrogen is saved because of the short interruptions between treatments. Aside from this, the cabin is quickly operational again after such pauses. It is also possible, during idling, to produce only a reduced amount of treatment gas for the purpose of keeping the cold wind apparatus and the supply lines cold.

Aside from the energy saving, such a method of operation also has the advantage that the patient does not have to be positioned in a cold environment. At the start of the treatment, the valves 21 and 22 are switched so that the treatment gas enters the interior of the cabin via nozzle strips 7.

The cabin is equipped with the customary safety devices which are, however, not shown. It is, here, a matter of an oxygen sensor in the area of the patient's head, which in case of a lack of oxygen in the breathable air, automatically causes the cooling operation to stop.

Furthermore, infra-red probes can be provided which allows continuous temperature monitoring of the patient's skin.

As was described at the beginning, the cabin is entered by means of a simple door. The installation of a lock is not necessary since the cabin is switched during pauses in treatment when idling whereby the air in the cabin warms up.

SUMMARY

Cryotherapy on the entire body with cold treatment gas in closed cabins has several disadvantages. These consist, on the one hand, of psychological barriers on the patient's part since, in spite of various communication media, direct contact between the physician and the patient is not possible. On the other hand, the unwanted cooling of the patient's head occurs and precautions must be taken to prevent the patient from inhaling the cold treatment gas. In order to avoid this deficiency, the cabin is open at the top and the walls 1, 2 or the floor are vertically adjustable so that the upper edge of the walls can be adjusted to be level with the neck of the patient. The treatment gas flows from the emanating devices located on the walls in the direction of the floor which is purposely designed as a grate 4 FIG. 1).

What is claimed is:

1. In a cabin for carrying out cryotherapy on an entire body of a patient with a cold treatment gas, the cabin having walls of insulating material, a door for entering the cabin, emanating devices for the treatment gas mounted on the walls, a return arrangement for the treatment gas, the improvement being in that said cabin is formed by a floor and by upstanding side walls having an upper edge spaced by a distance from the floor and by no top wall whereby said cabin is open from above to permit the head of the patient to extend above said cabin, said door being upstanding to create a closable vertical entrance into said cabin, and said distance from said upper edge of said walls to said floor of said cabin being adjustable to be level to the patient's neck.

2. Cabin according to claim 1, characterized therein that said floor is designed as a grate underneath which an outlet opening is provided.

3. Cabin according to claim 2, characterized therein that said walls are designed as consisting of two parts which can be slid against one another in a vertical direction.

4. Cabin according to claim 2, characterized therein that said floor can be adjusted in a vertical direction.

5. Cabin according to claim 2, characterized therein that said walls consist of double walled insulating material made of plastic.

6. Cabin according to claim 1, characterized therein that said walls are designed as consisting of two parts which can be slid against one another in a vertical direction.

7. Cabin according to claim 1, characterized therein that said floor can be adjusted in a vertical direction.

8. Cabin according to claim 1, characterized therein that said walls consist of double walled insulating material made of plastic.

9. In a process for carrying out cryotherapy on an entire body of a patient with a cold treatment gas wherein a cabin is used having insulated walls with gas treatment supply means mounted on the walls with the cabin having a return arrangement for the treatment gas and wherein the patient has a neck, the improvement being in forming the cabin from a structure consisting of a floor and upstanding side walls having an upper edge spaced by a distance from the floor and by no top wall whereby the cabin is open from above, manipulating the cabin structure to adjust the distance between the upper edge of the side walls and the floor until the upper edge is located at a distance corresponding to the neck of the patient, and directing the cold treatment gas into the cabin for contacting the entire body of the patient, except for the patient's head, with the cold treatment gas.

10. The process of claim 9 wherein the distance is adjusted by selectively raising or lowering the upper edge of the walls.

11. The process of claim 9 wherein the distance is adjusted by selectively raising or lowering the floor.

12. The process of claim 9 wherein the treatment gas flows from emanating devices on the walls downwardly into a return arrangement beneath the floor with the floor being in the form of a grate.

* * * * *